United States Patent [19]

Szinicz et al.

[11] 4,178,915
[45] Dec. 18, 1979

[54] SELECTIVELY OPERATABLE BLOCKING DEVICE FOR TUBULAR BODY ORGANS

[76] Inventors: Gerhard Szinicz; Werner Trawöger, both of Innsbruck, Austria, 6020

[21] Appl. No.: 825,104

[22] Filed: Aug. 16, 1977

[51] Int. Cl.² .................... A61F 1/00; A61B 17/00
[52] U.S. Cl. ...................... 128/1 R; 128/DIG. 25; 128/346
[58] Field of Search ............ 128/1 R, DIG. 25, 325, 128/326, 327, 346; 3/1

[56] References Cited

U.S. PATENT DOCUMENTS

| | | | |
|---|---|---|---|
| 3,744,063 | 7/1973 | McWaorter | 128/346 X |
| 3,854,469 | 12/1974 | Giori | 128/1 R |
| 3,863,622 | 2/1975 | Buuck | 128/346 X |
| 3,903,894 | 9/1975 | Rosen et al. | 128/DIG. 25 X |

Primary Examiner—Stephen C. Pellegrino
Attorney, Agent, or Firm—Karl F. Ross

[57] ABSTRACT

A device for selectively opening and closing a tubular body organ comprises a sleeve adapted to encircle the body organ and formed with a pressurizable compartment between inner and outer walls. The sleeve is connected by a duct to a supply vessel which is compressible to express a pressure medium into the sleeve by manipulation externally of the body. The supply vessel, which is implanted below the skin of the patient, is provided with means for retaining it in a compressed state, thereby retaining the blocked state of the body organ and preventing passage of a body material, e.g. feces or urine, therethrough. The latter means can be released to permit expansion of the supply vessel and hence return a fluid from the sleeve into the vessel.

22 Claims, 11 Drawing Figures

SELECTIVELY OPERATABLE BLOCKING DEVICE FOR TUBULAR BODY ORGANS

FIELD OF THE INVENTION

The present invention relates to a device for the selective blocking of natural or synthetic body organs and, more particularly, to a device operable externally of the body of an animal or human patient or subject, and adapted to selectively block or unblock a tubular organ so that, for example, the undesired passage of feces or urine can be prevented.

BACKGROUND OF THE INVENTION

In the treatment of human patients or in experimentel medicine, especially for the treatment of incontinence, it is desirable to provide means for selectively obstructing or obdurating the natural or synthetic tubular body organs through which certain body materials can pass. In the case of incontinence, it is desirable to block the uretha or other urine-passing duct while, in other cases, it is desirable to prevent the passage of solid and semi-solid wastes through portions of the intestine, the colon, or other ducts connected thereto.

Various devices for this purpose have been provided to enable, for example, a patient to control the passage of body materials through such natural and artificial tubular body organs. Such devices are designed to simplify the normal body functions. Such devices have utility where the normal constricting muscle system has been rendered inoperative by disease, operation or accident.

Such conventional devices can be subdivided into two groups. A first group comprises devices which are disposed externally of the body and provide a closure for the natural or synthetic body opening and can include a collecting vessel for the materials which are discharged. Typical of such devices are those disclosed in Austrian Pat. No. 172,942 and U.S. Pat. No. 2,423,060.

Such devices are not always satisfactory and certainly are less than aesthetic and desirable so that it has been considered important to provide the closure device within the body. The second group of conventional devices are designed to provide such internal closures. In general, these devices are intended to constrict synthetic or natural tubular body openings.

In some cases, this is accomplished by expanding (inflating) an elastic body inserted into the tubular body organ (see Austrian Pat. No. 169,094 and U.S. Pat. No. 2,324,520). A device of the last-mentioned type has been described in the publication Medical Tribune, Internationale Wochenzeitung-Ausgabe für Osterreich, No. 13, 1976, published by Medical Tribune GmbH, Wiesbaden, Germany.

The closure device here comprises an inflatable sleeve which is disposed around the portion of the intestine to be blocked and is connected by two conduits with a liquid supply vessel disposed also within the body but sufficiently close to a depressable portion thereof so that a balloon pump as well as a valve system can be actuated to effect transfer of fluid from the supply vessel to the sleeve and, via the valve system, from the sleeve into the supply vessel. Such devices have been found to be satisfactory in animal tests.

An important difficulty with this earlier system, however, resides in the complexity thereof and the relatively large number of parts, units or devices which must be implanted in the body, i.e. a sleeve, a supply vessel, two connecting conduits, two balloon pumps and valves. This not only makes the unit difficult to operate, but also creates problems with respect to reliability since the more complex the system, the less reliable it tends to be. Problems have also been encountered with such systems with respect to the failure of the seals at the connecting locations, wear and failure of the valves and the like. Furthermore, because of the large number of parts foreign to the body, there is an increased danger of infecton, necrosis and undesirable cell development around the inserted parts.

Another device which has been introduced into the body entirely is described in Volume 325, pp 1170–1174, of Langenbeck's Archiv fur klinische Chirurgie, Springer-Verlag, Berlin, Germany, 1969.

This device also comprises a pressurizable sleeve which is disposed around a tubular body organ. The sleeve is connected by a conduit to a micropump disposed in a housing and connected by a further conduit to a supply vessel which also can be disposed in the body. The micropump in the housing is electrically driven and the energy for operating this pump is transmitted thereto by a unit disposed outside the body and is picked up by an oscillator circuit (receiver) disposed in the housing of the micropump and supplied to the latter by an electric circuit. The direction of operation of the pump is also controlled by the transmitter.

This system also suffers from a disadvantage that a relatively large number of foreign bodies must be introduced into the human or animal organism, although the system has the advantage that valves are unnecessary. A further disadvantage of the latter system is that an external unit, namely the energy transmitter, is required for satisfactory functioning of the device. Should the patient lose the transmitter, or should the transmitter fail when the tubular body organ is blocked, its opening is not possible and the life of the patient as well as the patient's comfort are in danger.

OBJECTS OF THE INVENTION

It is the principal object of the present invention to provide a device for the aforedescribed purpose which has a minimum number of parts to be incorporated in the body and thus is less likely to cause infection, necrosis and undesired cell formation.

Another object of the invention is to provide a device for selectively blocking and unblocking a natural or synthetic body organ which obviates disadvantages of earlier devices for the same purpose.

Yet a further object of this invention is to reduce the operational complexity of a device for the selective blocking and unblocking of body organs.

It is still another object of this invention to provide a device of the character described which is more reliable, has a reduced number of moving parts, and a simpler construction than earlier systems.

SUMMARY OF THE INVENTION

These objects and others which will become apparent hereinafter are attained in accordance with the present invention by providing, as the fluid-displacing device for a sleeve of the type described, a fluid-pressure supply vessel which can be displaced between an expanded position and a compressed position and thus which has a variable volume so that the vessel itself, under compression, can displace the pressure medium into the organ-blocking sleeve. The vessel according to the invention is provided internally with means for retaining it in the compressed state and for releasing the latter means to enable the vessel to expand into its enlarged condition.

The organ-blocking device according to the invention thus comprises, in its main parts, a sleeve adapted to surround a natural or artificial body organ and which is pressurisable with a fluid member, a connecting duct communicating with this sleeve, and a fluid-displacing device which, according to an essential feature of the invention, constitutes the supply vessel for the pressure medium. The number of mechanically movable parts is thus reduced significantly by comparison with earlier systems and both valve and separate plumbing arrangements are eliminated by the provision of means within the supply vessel for releasably retaining the same in its compressed state.

The following advantages thus result:

(a) The operational complexity is reduced because of the similar number of parts by comparison with known organ-blocking units, thereby also reducing the complexity of the surgery necessary for implantation.

(b) The body reaction to the foreign elements introduced into the body of the patient is reduced.

(c) The reliability of the device is increased by the smaller number of parts and the probability of failure is reduced to a minimum, (d) There is a reduced danger to the patient because of failure of the system and repair or recovery from failure is simplified since the supply vessel only need be of concern and can be located directly below the skin of the patient, enabling a complete replacement or repair of the supply vessel with ease.

(e) No check valves or closure valves are required for the connecting conduits.

(f) The incorporation of electrically driven elements and their dependence upon external units such as a transmitter are eliminated.

The blocking device of the present invention functions as follows:

In the expanded state of the supply vessel, normal body pressure, at most, prevails in the sleeve which surrounds the tubular body organ. Preferably a slight sub-atmospheric pressure can prevail in the sleeve. The passage of body materials, e.g. urine or feces, through the tubular body organ in the region of the sleeve is not restricted. When it is desired to interrupt the passage of body materials, the supply vessel is compressed by pressing upon the skin in the region of the supply vessel, thereby displacing the flud pressure medium into the sleeve and raising the pressure therein. The flow cross-section of the tubular body organ is thereby constricted and can be reduced practically to zero, whereby a complete blockage or an approximately complete blockage of flow through the body organ results. The supply vessel is retained in its compressed state by the retaining means provided within the supply vessel. When the side of the supply vessel lying opposite the side proximal to the skin is provided with a stiffening plate, movement of the inner wall of the supply vessel upon pressure from the exterior is precluded.

By pressing slightly inwardly a second time, the compressed state can be released and the supply vessel permitted to expand, by the fluid pressure in the sleeve or by springs provided in the walls of the supply vessel, thereby increasing the volume of the supply vessel and permitting the fluid pressure in the sleeve to be drained. Preferably a slight sub-atmospheric pressure is thereby generated in the expandable compartment of the sleeve, whereby the flow cross-section of the body organ is again unconstricted and at its normal size for the passage of body substances.

According to another feature of the invention, the supply vessel has the configuration of a body of rotation whose axis is parallel to the direction in which the supply vessel is compressed to express the pressure medium, preferably a liquid, into the sleeve through the aforementioned conduit. The supply vessel can comprise a pair of frustoconical shells joined together along their edges at the broad bases of the shells by a sealing junction. The means for restoring the expanded state to the supply vessel can include at least one restoring spring provided in the supply vessel.

Advantageously, each of the shells is provided with at least one restoring spring and each restoring spring can lie substantially parallel to the walls of the respective shell. More specifically, each restoring spring can be embedded in a respective wall of the shell and at least one of the restoring springs can extend radially of the rotation axis of the vessel.

It has been found to be advantageous to provide the restoring spring with a star spoke, spider or claw configuration.

The restoring springs or at least one of the restoring springs can be composed of a material which is inert to the body substances, and to the fluid pressure medium. Each of the shells can comprise two layers of elastic material between which the respective restoring spring is sandwiched.

According to another feature of the invention, the means for retaining the compressed state of the vessel includes a male formation disposed on one side of the supply vessel and a female formation disposed on the opposite side of the vessel and receiving the male formation upon compression of the supply vessel, i.e. displacement of the one side of the vessel toward the opposite side. The male and female formations can extend from the opposite walls of the supply vessel toward the interior thereof in the expanded state of the vessel and one of the formations can be provided with a spring-loaded pin lying perpendicular to the compression direction and engageable in a recess in the other formation.

Advantageously, the pin is provided in the female formation, while the recess is provided in the male formation. The recess can provide a track in which the pin is guided and which can form at least one step in the direction in which the pin spring is effective. The guide track can have a heart-shaped configuration and can be provided at each inflection point with a step. The guide track can also be formed, between two steps, with a rise which is effective in the direction opposite that in which the pin spring is effective.

The pin can be composed of hardened steel in accordance with still another feature of the invention and we have found it to be advantageous to make the supply vessel of such size that the change in volume between the expanded and compressed states thereof lies between 10 and 30 ml. For practical operation of the device it has been found to be advantageous to so construct the latter that between the expanded and the compressed state of the supply vessel, a pressure differential is generated at the sleeve which lies between 50 and 200 cm. of water column. This pressure differential preferably ranges between 60 and 120 cm. of water column.

The supply vessel may also be provided with a closable filling duct which lies directly beneath the skin of the patient provided with the device.

It has been found to be advantageous, as noted previously, to provide the side of the supply vessel which is disposed toward the interior of the body of the patient with a stiffening plate which retains this side of the supply vessel against movement upon the application of pressure from the exterior. The supply vessel may be provided with a hand grip on its side turned toward the skin of the patient. The hand grip can also be formed by a plate disposed on this side of the supply vessel turned toward the exterior.

While we prefer to provide restoring springs as described above, it is also contemplated within the context of the present invention to eliminate these springs and permit the pressure of the medium within the sleeve to restore the supply vessel to its expanded state.

For simplicity of implantation, operation and access, the supply vessel should be surgically inserted in the hip region of the patient.

BRIEF DESCRIPTION OF THE DRAWING

The above and other objects, features and advantages of the present invention will become more readily apparent from the following description, reference being made to the accompanying drawing in which.

SPECIFIC DESCRIPTION

Figure 1:
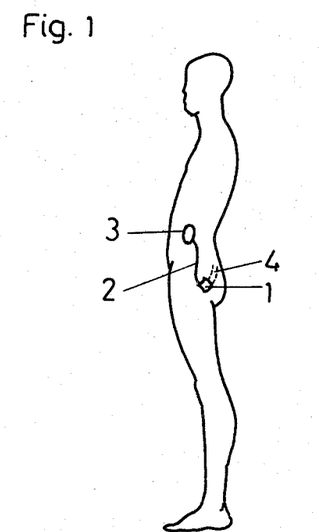
FIG. 1 is a schematic diagram illustrating the arrangement of the organ-blocking device of the present invention in a human body.

The device illustrated in FIG. 1 in diagrammatic form comprises a blocking unit for selectively closing an intestinal or other lower body passage. The blocking device consists basically of three elements, the sleeve 1, which extends around the tubular body organ 4, the connecting duct 2, and a pressure medium supply vessel 3 which also serves as the displacement device for the pressure medium.

Figure 2:
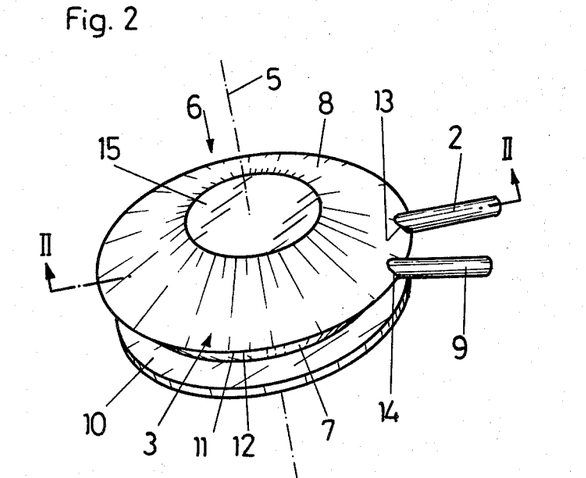
FIG. 2 is a perspective view of a supply vessel embodying the present invention.

The pressure medium supply vessel has been shown in FIG. 2 in enlarged perspective and comprises a body of rotation whose rotation axis 5 lies parallel to the direction of compression represented by the arrow 6.

The supply vessel 3 is formed from a pair of frustoconical shells 7 and 8 which have their broad bases on edges 11 and 12 sealed together.

At an appropriate location 13, preferably in the region of the edge 11, 12, the connecting duct 2 communicates with the interior of the vessel. The tube 2 is preferably a flexible hose and runs to the sleeve 1. At another location 14, a filling duct 9, preferably also a flexible hose, provided with a closure not shown communicates with the supply vessel 3. The filling duct is so constructed that it lies directly below the upper surface of the skin. The vessel 3 is implanted in the hip region of the patient.

A stiffening plate 10 is fastened to the shell 7 of the supply vessel 3 and serves as a support for the surface or side of the vessel 3 which is turned toward the interior of the body. This support prevents displacement of the internal side of the vessel when pressure is applied to the outwardly turned side thereof.

The shell 8 is also formed with a plate which constitutes a coaxial grip 15 turned toward the skin of the patient. The handle 15 serves to enable the supply vessel 3 to be readily located below the skin of the user.

Figure 3:
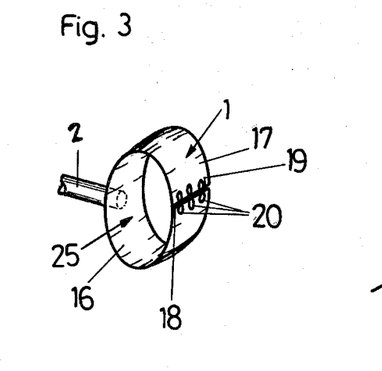
FIG. 3 is an enlarged perspective view of a sleeve adapted to fit around the body organ to be blocked, the sleeve being shown in its operative position.

As can be seen from FIG. 3, the sleeve 1 can surround a tubular body organ. The other wall 17 and the inner walls 16 of the sleeve 1 define a pressure compartment between them, the connecting duct 2 from the supply vessel 3 communicating with this compartment.

Figure 4:
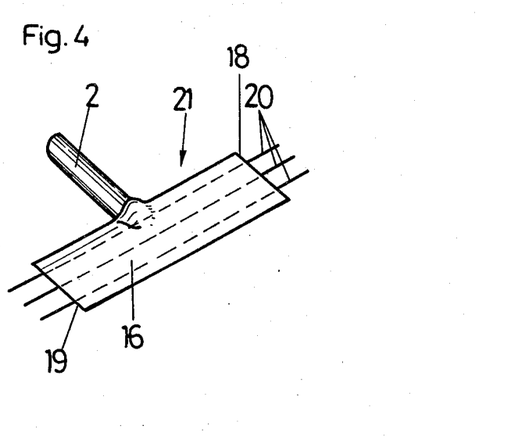
FIG. 4 is a view drawn to the same scale as FIG. 3 but illustrating the blocking device before it is formed into its sleeve configuration.

As can be seen from FIG. 4, the sleeve 1 may be formed originally as a band with the outer wall 17 and the inner wall 16 being constituted as respective strips 21 whose ends 18 and 19 can be connected together. In the embodiment illustrated, this connection can be effected by threads 20, inert to the components of the human body, which can extend beyond the ends 18 and 19 and can be tied together, these threads 20 being embedded in the outer and/or inner walls 16 and 17.

All the components of the sleeve can be constituted of an elastic material inert to body substances. We have found that best results are obtained with the high-polymer elastic organo-silicon compound marketed under the name SILASTIC by Dow Corning, Midland, Ohio, U.S.A., this elastomeric material being white, rubber-like and water-repellent. The elongation of the material is 70–115% and these characteristics are retained in a temperature range between +260° C. and −90° C.

Figure 5:
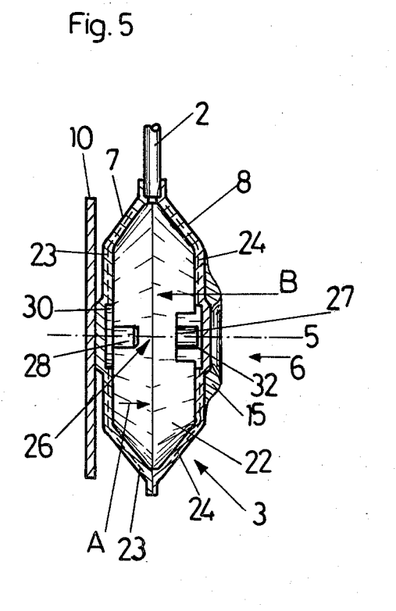
FIG. 5 is a cross-sectional view taken generally along the line II—II of FIG. 2 through the supply vessel.

FIG. 5 shows a section through the supply vessel 3 parallel to the axis the body of revolution 5.

The two shells 7 and 8 of the supply vessel 3 are symmetrical with respect to a plane perpendicular to the axis 5 and define an internal chamber 22 whose volume is variable.

FIG. 5 shows the supply vessel in its expanded state, i.e. the chamber 22 has its maximum volume in the position shown in FIG. 5. To reduce the volume, the supply vessel 3 is compressed in the direction of the arrow 6, the stiffening plate 10 serving as a support preventing displacement of the left-hand side of this vessel 3. For restoring the supply vessel 3 from its compressed state to the expanded state shown in FIG. 5, we prefer to provide a pair of restoring springs 23 and 24 which are embedded in the walls of the shells 7 and 8 and one of which has been shown in plan view in FIG. 6.

Upon reduction of the volume of the chamber 22, the pressure medium contained therein is displaced via the duct 2 into the sleeve 1 whose throughgoing opening 25 is thereby reduced. The result is a constriction of the tubular body organ 4 substantially to reduce its cross-section to zero.

Within the supply vessel 3 we provide, coaxial to the rotation axis 5, means generally designated at 26 which, upon a first compressive movement of the shell 8 from the position shown in FIG. 5 in the direction of arrow 6, retain the supply vessel 3 in its compressed position. After a slight second movement in the direction of the arrow 6, the shell 8 is freed (i.e. is released) and can be biased into its expanded position by means of the restoring springs 23,24. This draws the fluid in the sleeve 1 through the duct 2 into the enlarged chamber 22 and reduces the pressure in the sleeve 1. The cross-section 25 of the sleeve is thereby enlarged and the constriction of the body organ is removed.

The retaining means 26 for holding the vessel 3 in its compressed state comprises a male formation 28 which is provided on the shell 7 and a female formation 27 into which the male formation 28 can pass. The female formation 27 is provided upon the shell 8.

Figure 6:
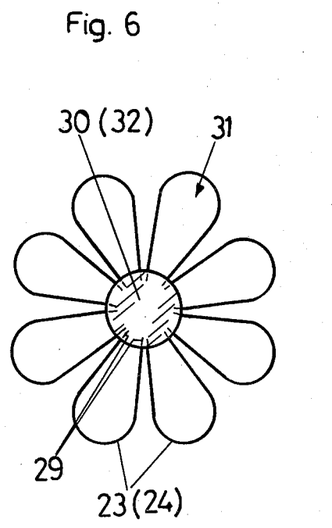
FIG. 6 is a plan view of a restoring spring for use in the supply vessel of FIGS. 2 and 5.

The restoring spring 23,24 illustrated in FIG. 6 and represented as a unit at 31, comprises a star or spider shaped structure which has a somewhat U-shaped bend (see FIG. 5) and can be composed of spring wire of an appropriate synthetic resin or material. Further details of the spring will be apparent from FIG. 7. The spring wires can have ends 29 which are received in substantially radial bores 35 of a support plate 30, 32.

In the walls of each shell 7,8 is received a respective set of restoring springs 23,24 including the support plates 30 and 32, the support plates 30 and 32 simultaneously serving as carriers for the female formation 27 and the male formation 28.

In the expanded state, the restoring springs 23 and 24 are so bent that their curvature or shape corresponds to the shape of the shell 7,8 in the expanded state.

Figure 7:
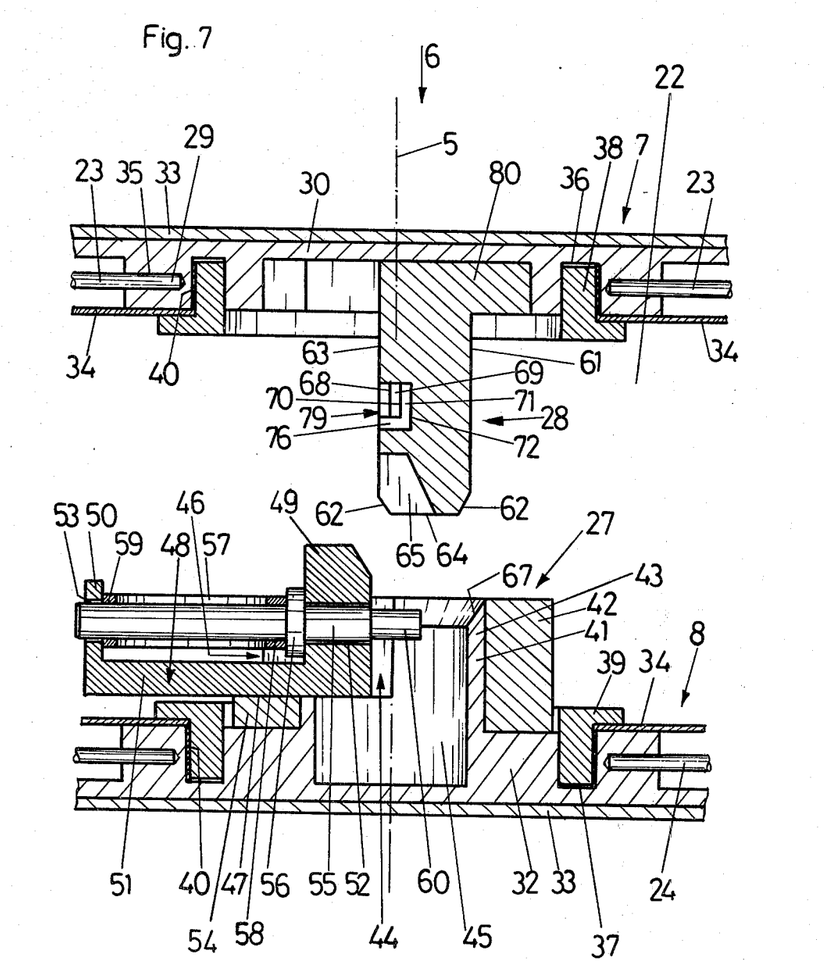
FIG. 7 is a detail view in axial cross-section and drawn to an enlarged scale of the retaining means for holding the supply vessel in its compressed state.

As can be seen in detail from FIG. 7, which represents a section similar to that of FIG. 5 but drawn to an enlarged scale to show only the central region of the supply vessel 3, each shell 7,8 is formed in two layers and comprises an outer layer 33 and inner layer 34 of an elastomeric material which is inert to body substances. Preferably this material is constituted by the SILASTIC silicone elastomer described above. The springs 23 and 24 are received between the outer layer 33 and the inner layer 34.

The outer layer 33 extends over the carrier plates 30 and 32 while each inner layer 34 can have an opening coaxial with the axis 40 with the inner edge of this opening clamped in angular groove 36,37 of the support plate 30,32 and held therein by press-fitted rings 38 and 39.

Along the edges 11, 12 of the shell 7,8, the two outer layers 33 and the two inner layers 34 are sealingly connected together, preferably by an adhesive or by thermal welding.

The pressure medium within the chamber 22 thus is not able to penetrate between the two layers 33 and 34, nor can it pass out of the supply vessel 3 except through the conduit 2. A sealed fitting connected to the junction between the edges 11 and 12 serves to connect the conduit 2 to the supply vessel. A similar fitting can be used to connect the filling conduit thereto. The hoses 2 and 9 can of course, also be connected directly to the supply vessel, i.e. by welding or adhesive bonding.

The female part 27 (lower half of FIG. 7) comprises an inner sleeve or boss 41 which projects from its support plate 32 and has a transition into a projection 43 extending over about 180°. The projection 43 thus has the configuration of half of a longitudinally subdivided sleeve and defines a radial opening 44 in the socket compartment 45 within the sleeve 42 extending around the inner sleeve 41 and the axial projection 43 therefrom and has a radial opening 46 which is flush, i.e. registers, with the radial opening 44.

The boundary surface of the cutout 46 forms a contact face 47 and a substantially U-shaped insert 48 which rests with its web 51, connecting the two radial shanks 49 and 50, upon the face 47.

The two radial shanks 49 and 40 are each provided with a respective passage 52,53. Lateral shank 49 of insert 48 extends into the socket space 45 through the cutout 46 and the opening 44 and rests on shoulder 54 of the outer sleeve 42.

The opening 52 of shank 49 is formed as a slit while the opening 53 of shank 50 is formed as shown. Both serve as supports for a spring-loaded pin 55 of hardened steel. Because of the slit-like opening 53, the pin 55 has a limited pivotal mobility in a plane perpendicular to the axis 5 of the vessel 3.

The pin 44 has an annular shoulder 56 against which a spring 57 bears, the spring 57 being formed as an elastic ring having bores 58 and 59 traversed by the pin 55.

The spring 57, at its side diammetrically opposite bore 58 is set against the radial shank 50 of the insert 48. Firstly the spring 57 biases the pin 55 in the direction of the socket chamber 45 within the sleeves 41,42 so that a projecting end 60 of the pin 55 lies within the socket chamber.

FIG. 7 shows, as has already been indicated, the expanded state of the supply vessel 3. In this state, the male formation 28 does not engage in the female formation 27 and the two formations are spaced apart.

Figure 8:
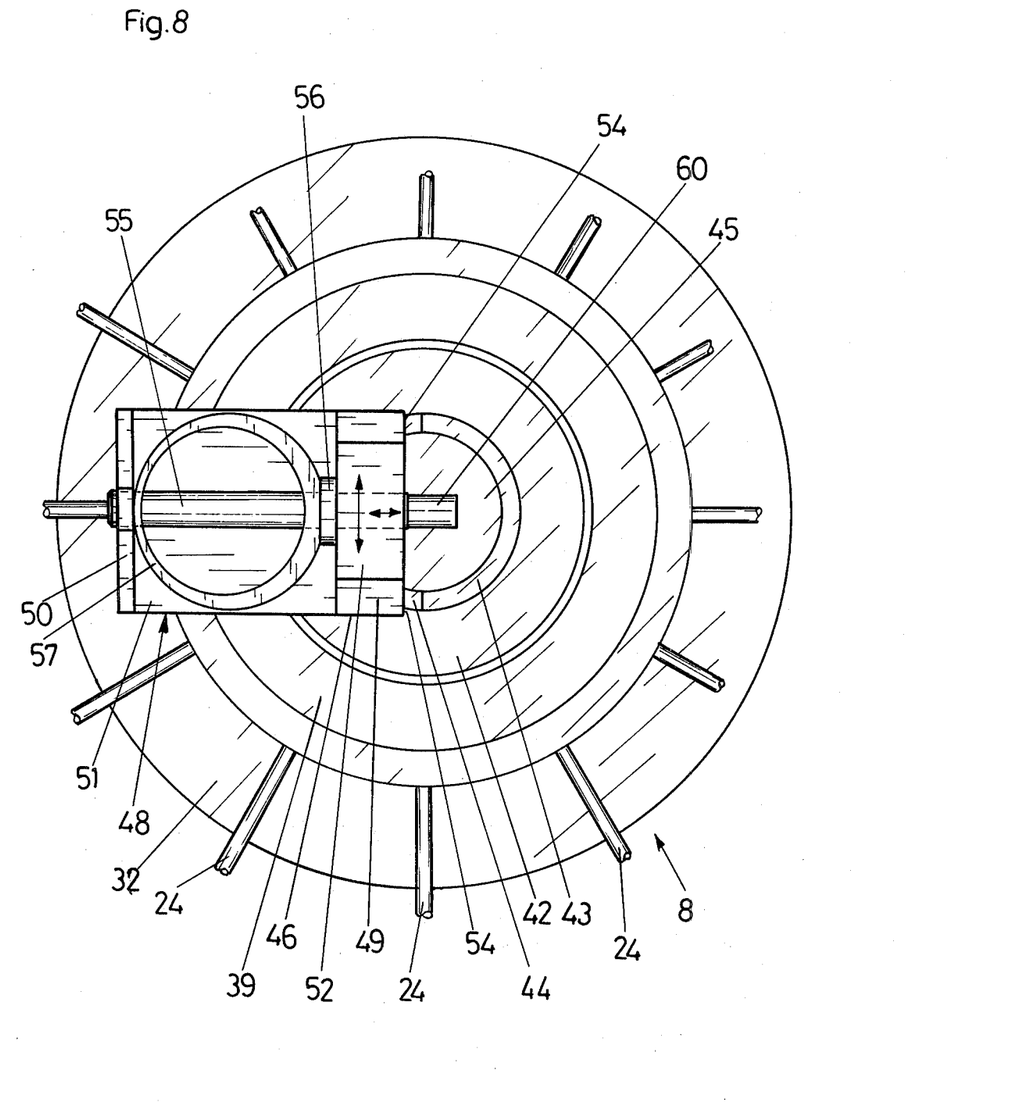
FIG. 8 is a plan view of one portion of this retaining means.

As can be seen from FIG. 8 which represents a plan view of the female formation 27 taken in the direction of arrow A of FIG. 5, the springs 57 has its greatest thickness proximal to the projecting end 60 as its engagement with the shoulder 56. The spring tapers down in cross section toward the opposite end at which it is seated against the shank 50 of the insert 48.

Figure 9:
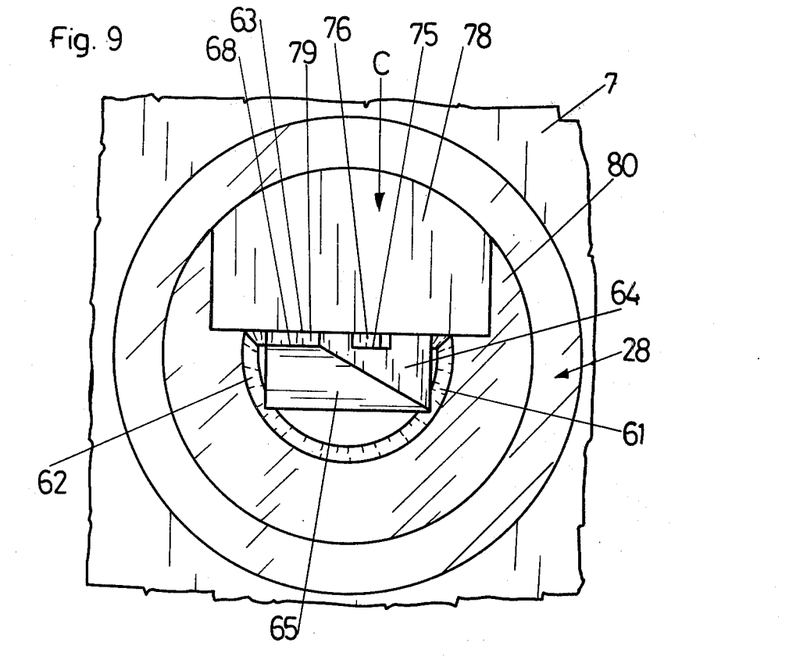
FIG. 9 is a plan view of another portion of this retaining means.
Figure 10:
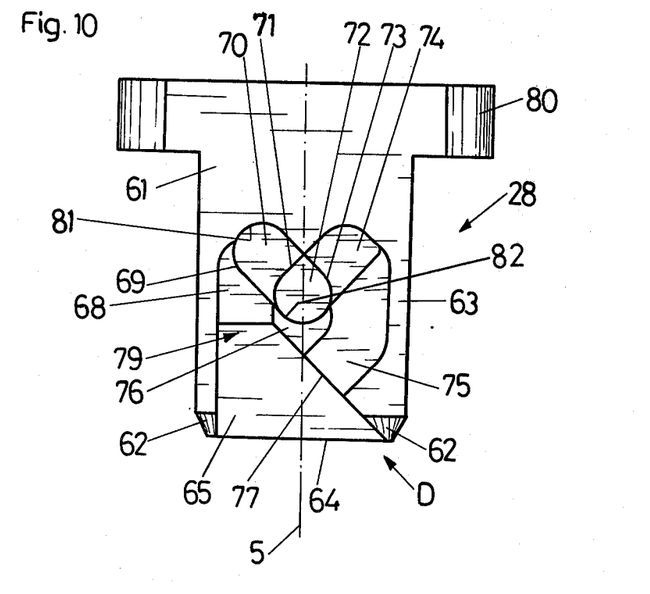
FIG. 10 is a side elevational view taken in the direction of arrow C of FIG. 9.
Figure 11:
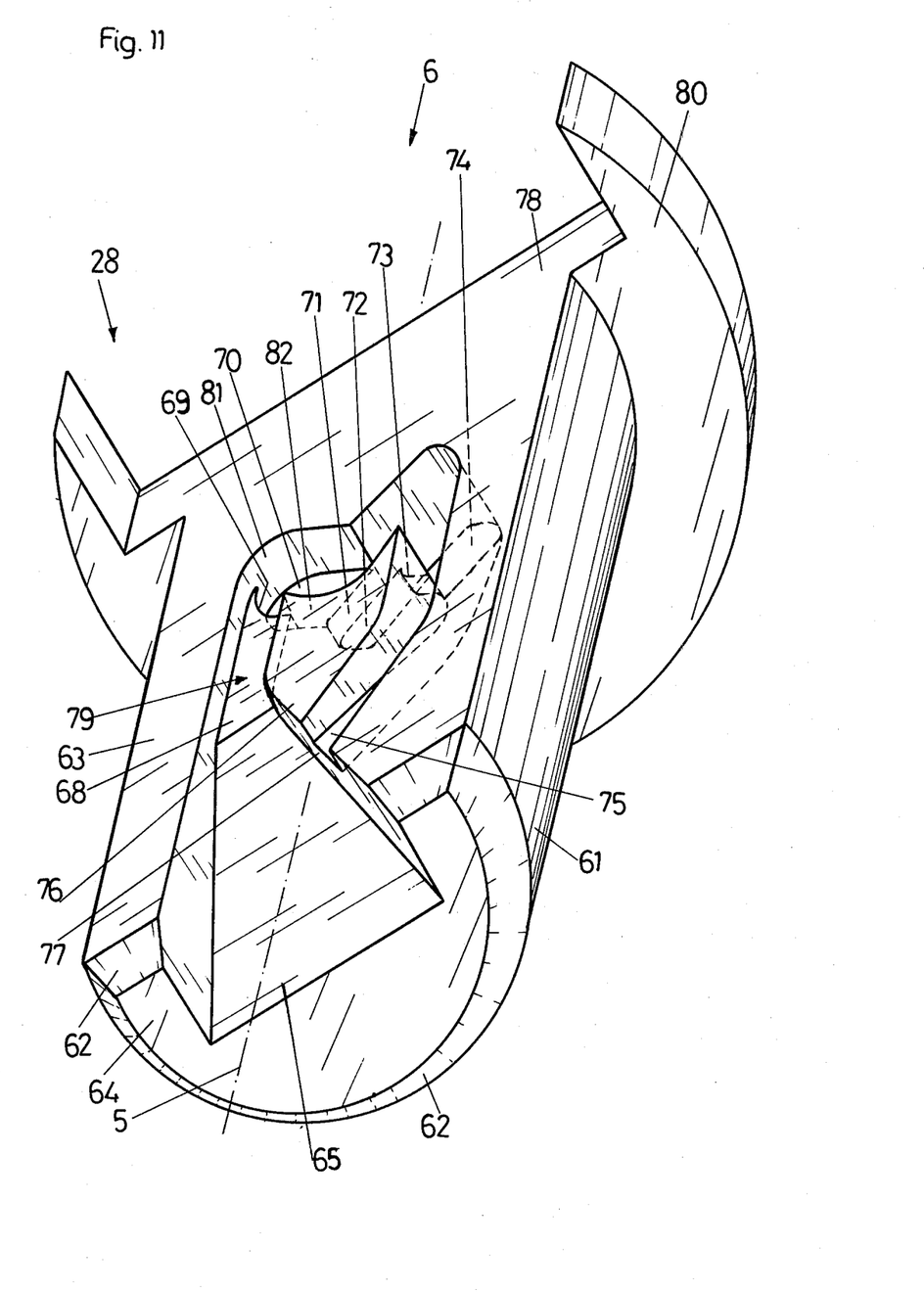
FIG. 11 is a perspective view taken in the direction of arrow D of FIG. 10.

The functioning of the mechanism to retain the compressed state of the vessel will become more readily understandable from the following description with respect to FIGS. 9 through 11 which deal with the male formation 28.

The male formation 28 comprises a substantially semicylindrical part 61 and a flange 80 which is seated in the support plate 20 of shell 7. The free end 64 of the semicylindrical part 61 is pivotal at 62 to facilitate insertion to the female formation 27.

The semicylindrical part 61 has a planar surface 63 which extends parallel to the axis 5 and is formed, e.g. by milling, with a guide track 79 adapted to receive the projecting end 60 of the pin 55. The guide track 79 has a generally heart shape with the point of the heart turned toward the free end 64 of the semicylindrical part 61 and widening in this direction to form a mouth 65 to facilitate the guidance of the pin into the track.

At the inflection points of the heart-shaped track 79 steps 69, 71, 73 and 77 of reduced height in a direction perpendicular to the axis 5, are provided.

Upon compression of the supply vessel 3, the two shells 7 and 8 move relative to one another in the direction of arrow 6 and the male formation 28 projects into the socket 45 of the female formation 27. Centering of the two formations is effected automatically by means of the beveled edge 62 of part 61 and/or an internal bevel 67 of the sleeve 43. Further centering can be ensured by beveling the inner shank 49 of the insert 48.

With further penetration of the male formation 28 and its part 61 in the direction of arrow 60 into the female formation, the end 60 of the pin 55 rides along the inclined surface or ramp of the mouth 65 of track 79 and is thereby biased against the force of its spring 57. The pin is thus shifted radially outwardly and perpendicular to the axis 5.

Further displacement of the male formation in the direction of arrow 6 causes the end 60 of pin 55 to ride along the first guide surface 68 in the direction of flange 80 until it engages the flank 81 bounding the track 79. Immediately before reaching this flank, the end 60 of pin 55 engages the first step 69 and is thus pressed against the second guide surface 70 by the force of the spring.

The compressive operation of the supply vessel 3 is thereby terminated and the desired constriction pressure prevails in the sleeve 1, the compressed state of the vessel 3 being retained by the engagement of the pin with the male member.

In this retained state, the end 60 of the pin 55 rests upon the first step 69 so that its return movement along the guide surface 68 is prevented although movement along the second guide surface 70 remains possible.

The end 60 of pin 55 is guided along the second guide surface 70 and the lateral flank 82 of the central piece 76 onto the second step 71 which is recessed more deeply in the track so that the spring 57 can press the pin 55 more deeply into the latter and onto the third guide surface 72. This is, in the direction of compression 6, the deepest point of the tract 79 and the final position for the compressed state. During the movement from the upper inflection point along flank 81 to the end position, the supply vessel 3 is slightly expanded so that the desired operating pressure is applied to the closure sleeve. Prior thereto, as will be apparent, the more compressed state of the vessel causes a slightly higher pressure than the desired operating pressure to prevail in the sleeve. An automatic further movement of the end 60 of pin 55 is prevented by the concave curvature of flank 82 of the central piece 76.

Should it be desired to reduce the pressure in the sleeve 1 surrounding the tubular body organ, the supply vessel 3 is further compressed slightly in the direction of arrow 6. The end 60 of pin 55 is thereby guided along the third guide surface 72 over the third step 73 since the second step 71 blocks return movement along the second guide surface 70. The spring 57, after the end 60 of pin 55 clears the third step 73, presses the pin against the fourth guide surface 74. In this position further compression of the supply vessel 3 is precluded since the end 60 of pin 55 lies against the second upper inflection point of the boundary flank 81.

Since the pressure in the direction of arrow 6 is released as soon as the patient removes his hand from pressing contact with the skin in the region of the supply vessel, the restoring springs 23 and 24 bias the shells 7 and 8 relatively apart. The return of the end 60 of pin 55 along the third surface 72 is blocked by the third step 73. Thus the end 60 can only move along the fourth guide surface 74 level with the guide surface 75 into its original position, i.e. to the mouth 65. The fifth guide surface 75 rises toward the end 60 of pin 55 and thus displaces the latter against the force of its spring 57.

At the end of the fifth guide surface 75 there is provided a fourth step 77 which prevents reverse movement of the pin from the mouth 65 upon the next compression of the supply vessel 3 so that the end of the pin 60 slides along the first guide surface 68 and does not return to the fifth guide surface 75. Further expansion withdraws the part 61 completely from the female part 27 and hence restores the vessel to the position shown in FIG. 5.

The organ-blocking device of the present invention is disposed entirely in the body with the sleeve around the body organ to be obturated and the supply vessel and its filling hose in the hip region directly beneath the skin to facilitate repair or replacement of the supply vessel. The system can be emplaced with a minimum or surgery.

It is important to note that danger to the patient because of prolonged closure of the body organ is reduced since the means for retaining the compressed state remain engaged while a small incision can free the filling conduit and its closure (not shown) so that the liquid medium in the sleeve can be drained and the obstruction at least partially removed.

In human medicine, we have found that the change in volume between the expanded and compressed state of the supply vessel should be between 10 and 30 ml while the pressure differential between these states should be between 60 and 120 mm water column. For use in experimental medicine, larger ranges may be employed.

The fluid pressure medium can be distilled water or organic liquids for example, liquid paraffin. We have found low viscosity paraffin (paraffin perliquidum) to be most effective. This liquid consists of a mixture of high purity saturated hydrocarbons which are odorless and tasteless, clear, colorless, oily and nontoxic with a density of 0.83–0.87 and a maximum viscosity of 65 cP.

The supply vessel 3 can also be enclosed in an outer sheath, not shown, of the aforementioned SILASTIC silicone elastomer.

In a simplified version of the device of the present invention, the restoring springs 23 and 24 are omitted and the elastic force of the sleeve 1 is used to drive the liquid back into the supply vessel when the latter expands. The passage of the body substance through the previously constricted organs can bring about the final expulsion of the liquid from the sleeve.

While this invention has been described in detail with respect to an embodiment above, it should be understood that the invention also comprehends all equivalent structures within the spirit and scope of the appended claims and, particularly, the means for retaining the vessel in the compressed state need not be restricted to the male and female members described unless set forth in the claims.

We claim:

1. A closure device for the selective blocking and unblocking of a tubular body organ, said device comprising:
   a sleeve surrounding said body organ within the body of a subject, said sleeve being formed with an expandable compartment;

a connecting duct communicating with said compartment and disposed within the body of said subject;

a variable-volume supply vessel containing a pressure medium and communicating with said sleeve, said vessel being disposed within the body of said subject and being actuatable between a compressed state and an expanded state, said vessel being formed from a pair of shells sealingly interconnected along their edges;

means within said vessel for releasably retaining said vessel in said compressed state; and restoring means in said vessel for biasing same into said expanded state.

2. The device defined in claim 1 wherein said supply vessel has the configuration of a body of revolution with an axis extending in the direction of compression of said vessel.

3. The device defined in claim 1 wherein said restoring means includes at least one restoring spring disposed in said vessel.

4. The device defined in claim 3 wherein each of said shells is provided with at least one restoring spring.

5. The device defined in claim 3 where each of said restoring springs extends parallel to a respective shell of the vessel.

6. The device defined in claim 4 wherein each of said springs is disposed within the wall of a respective shell.

7. The device defined in claim 3 wherein at least one of said springs extends radially with respect to said axis.

8. The device defined in claim 3 wherein each of said springs has a substantially star configuration.

9. The device defined in claim 3 wherein each of said springs is composed of a material inert to said medium and to body substances.

10. The device defined in claim 1 wherein each shell consists of two layers of elastic material with a respective restoring spring disposed between said layers.

11. The device defined in claim 1 wherein the volume change between said states of said vessel is between 10 and 30 ml.

12. The device defined in claim 1 wherein the pressure differential in said medium between said states is 50 to 200 cm water column.

13. The device defined in claim 12 wherein the pressure differential is between 60 and 120 cm water column.

14. The device defined in claim 1 wherein said vessel has a side turned toward the interior of the body of said subject and a side turned toward the skin of the subject, said side turned toward the interior being provided with a stiffening plate.

15. The device defined in claim 14 wherein the side of said vessel turned toward the skin is provided with a hand grip in the form of a plate.

16. A closure device for the selective blocking and unblocking of a tubular body organ, said device comprising:

a sleeve surrounding said body organ within the body of a subject, said sleeve being formed with an expandable compartment;

a connecting duct communicating with said compartment and disposed within the body of said subject;

a variable-volume supply vessel containing a pressure medium and communicating with said sleeve, said vessel being disposed within the body of said subject and being actuatable between a compressed state and an expanded state;

means within said vessel for releasably retaining said vessel in said compressed state, said retaining means including a male formation on one side of said vessel and a female formation on the opposite side of said vessel, said male formation being receivable in said female formation upon compression of said vessel, one of said formations being provided with a spring-loaded pin extending in a direction perpendicular to the direction of compression of said vessel and the other of said formations being formed with a recess receiving said pin.

17. The device defined in claim 16 wherein the pin is provided in said female formation and the recess in said male formation.

18. The device defined in claim 16 wherein said recess is formed as a track provided with steps acting upon said pin in a direction opposite to that upon which a spring bears against said pin.

19. The device defined in claim 18 wherein said track has a heart-shaped configuration which is formed at inflection points with respective steps.

20. The device defined in claim 19 wherein said track rises toward said pin between two of said steps.

21. The device defined in claim 16 wherein said pin is composed of hardened steel.

22. A closure device for the selective blocking and unblocking of a tubular body organ, said device comprising:

a sleeve surrounding said body organ within the body of a subject, said sleeve being formed with an expandable compartment;

a connecting duct communicating with said compartment and disposed within the body of said subject;

a variable-volume supply vessel containing a pressure medium and communicating with said sleeve, said vessel being disposed within the body of said subject and being actuatable between a compressed state and an expanded state;

means within said vessel for releasably retaining said vessel in said compressed state; and a closable filling conduit communicating with said vessel and having a mouth disposed directly in the skin of said subject.

* * * * *